US00PP13186P2

(12) United States Plant Patent
Utecht

(10) Patent No.: US PP13,186 P2
(45) Date of Patent: Nov. 5, 2002

(54) GERANIUM PLANT NAMED 'FISTABLANC'

(75) Inventor: Angelika Utecht, Montabaur (DE)

(73) Assignee: Florfis, AG, Binningen (CH)

( * ) Notice: Subject to any disclaimer, the term of this patent is extended or adjusted under 35 U.S.C. 154(b) by 0 days.

(21) Appl. No.: 09/989,121

(22) Filed: Nov. 21, 2001

(65) Prior Publication Data

US 2002/0083499 P1 Jun. 27, 2002

(51) Int. Cl.[7] ..... A01H 5/00

(52) U.S. Cl. ..... Plt./326

(58) Field of Search ..... Plt./326

*Primary Examiner*—Kent L. Bell
(74) *Attorney, Agent, or Firm*—Foley & Lardner

(57) ABSTRACT

A new and distinct cultivar of geranium plant named 'Fistablanc', as described and illustrated herein and particularly characterized by the combined features of white, semi-double flowers, medium sized umbels well above the foliage, dark-green foliage with slight zonation on young leaves, medium sized, round plant habit, and moderately early flowering.

1 Drawing Sheet

BOTANICAL CLASSIFICATION

*Pelargonium zonale.*

VARIETY DENOMINATION

'Fistablanc'.

BACKGROUND OF THE INVENTION

The present invention comprises a new and distinct cultivar of geranium, botanically known as *Pelargonium zonale*, and hereinafter referred to by the cultivar name 'Fistablanc'.

'Fistablanc' is a product of a planned breeding program which had the objective of creating a new geranium variety with white flower color and medium sized plant habit in combination with dark-green foliage, and at least a trace of zonation.

'Fistablanc' originated from a hybridization made by the inventor Angelika Utecht in a controlled breeding program in Galdar, Gran Canaria, Spain, in 1996. The female parent was a commercial variety 'Glacis' (unpatented) which is similar to 'North Star' (U.S. Plant Pat. No. 9,971) having white, round semi-double flowers, floriferous habit, medium-green foliage and moderately vigorous growth. The male parent of 'Fistablanc' was an unpatented hybrid seedling no. K93-744-5, with white, single-type flowers, dark-green foliage with distinct zonation, and medium-sized plant habit.

'Fistablanc' was selected as one flowering plant within the progeny of the stated cross by Angelika Utecht in the spring of 1997 in a controlled environment in Galdar, Gran Canaria, Spain.

The first act of asexual reproduction of 'Fistablanc' was accomplished when vegetative cuttings were taken from the initial selection in the fall of 1997 in a controlled environment in Galdar, Gran Canaria, Spain, by, or under the supervision of Angelika Utecht. Horticultural examination of plants grown from cuttings of the plant initiated in May 1998 in Hillscheid, Federal Republic of Germany, and continuing thereafter, has demonstrated that the combination of characteristics as herein disclosed for 'Fistablanc' are firmly fixed and are retained through successive generations of asexual reproduction. The new cultivar reproduces true to type.

'Fistablanc' has not been observed under all possible environmental conditions. The phenotype may vary significantly with variations in environment such as temperature, light intensity and day length.

The following observations, measurements, and comparisons describe plants grown in Hillscheid, Germany, and in Langley, British Columbia, Canada, under greenhouse conditions which approximate those generally used in commercial practice.

BRIEF DESCRIPTION OF THE INVENTION

The following traits have been repeatedly observed and are determined to be basic characteristics of 'Fistablanc' which in combination distinguish this geranium as a new and distinct cultivar:

1. Large, white, semi-double flowers;

2. Semi-spherically shaped umbels, well above the foliage;

3. Dark-green foliage with weak zonation on young leaves;

4. Medium sized, round and uniform plant habit; and

5. Early to medium spring flowering response.

Of the many commercial cultivars known to the present inventor, the most similar in comparison to 'Fistablanc' are the patented varieties 'Floscala' (U.S. Plant Pat. No. 9,796) and the female parent 'Glacis'.

In comparison to 'Floscala', 'Fistablanc' has larger and differently shaped flowers, rounder and slightly more compact plant habit, inflorescences borne higher above the foliage, and slightly more compact plant habit. Flowers of 'Fistablanc' tend not to develop a pink hue.

In comparison to 'Glacis', 'Fistablanc' has more zygomorphic, rather than round flowers and dark-green foliage.

BRIEF DESCRIPTION OF THE DRAWINGS

The accompanying photographic drawing shows typical flower and foliage characteristics of 'Fistablanc' with colors being as true as possible with an illustration of this type.

The photographic drawing shows a flowering pot plant in a 14 cm container.

DETAILED BOTANICAL DESCRIPTION

In the following description color references are made to The Royal Horticultural Society Colour Chart (R.H.S.). The color values were determined indoors from plants growing in a green-house in May 2000, in Hillscheid, Germany. The measurements were taken in Langley in early July 2001, 18 weeks after planting of rooted cuttings. The plants were growing in 8 inch containers and had not been pinched.

Inflorescence:
- *Type*.—Umbel.
- *Shape*.—Semi-spherical.
- *Average diameter*.—120 mm.
- *Average depth*.—68 mm.
- *Peduncle length*.—206 mm.
- *Peduncle color*.—Light green, RHS 143 B.
- *Pedicel length*.—28 mm.
- *Pedicel color*.—Light green, RHS 143 B.
- *Number of flowers per umbel*.—About 25–35.
- *Lastingness of the umbel*.—About 18 days.

Corolla:
- *Average diameter*.—51 mm.
- *Form*.—Semi-double.
- *Shape*.—Zygomorphic, with a gap between upper and lower petals.
- *Number of petals*.—Average 10.1.
- *Petaloids*.—1–2, narrow, white, RHS 155 D (Both surfaces).
- *Shape of petals*.—Upper petals are narrow obovate, lower petals are obovate, base attenuate, upper end is rounded, margin is mainly entire, with slight crenation at the apex.
- *Size of petals*.—Upper petals: length 28–30 mm, width 19–20 mm. lower petals: length 26–28 mm, width 20–22 mm.
- *Color* (*general tonality from a distance of three meters*).—Pure white.
- *Color of upper and lower petals*.—RHS 155 D.
- *Base of upper petals*.—RHS 4 D.
- *Markings of upper and lower petals*.—None.
- *Color of lower surface of petals*.—RHS 155 D.
- *Color of sepals*.—Outer surface light green, RHS 144 A; inner surface: light green, RHS 144 B.
- *Number of sepals*.—5.
- *Shape of sepals*.—Linear to lanceolate, acute tip, truncate base, surface with very short pubescence, margin entire.
- *Size of sepals*.—11–12 mm long, 4 mm wide for the largest upper sepal, 2–3 mm in width for the other sepals.

Bud: (just before petals unfold):
- *Shape*.—Elliptical to narrow elliptical.
- *Color* (*lower part, sepals*).—Light green, RHS 144 A.
- *Color* (*upper part, petals*).—White to cream, RHS 155 D to RHS 4 D.
- *Length*.—22 mm.
- *Width*.—10 mm.

Reproductive organs:
- *Androecium*.—5–7 fertile anthers; white filaments, RHS 155 A, moderate pollen, orange, RHS 30 A.
- *Gynoecium*.—One pistil per flower, style and stigma cream colored, RHS 158 D, 5 to 6-lobed stigma.
- *Fertility/seed set*.—No seed set observed.

Spring flowering response period: In Hillscheid, Germany in 2000, plants had on average 1.2 flowers open 9 weeks after planting of rooted cuttings.

Outdoor flower production: Moderately rich and continuously flowering, the flower count in 2000 in Hillscheid, Germany, was about 3 inflorescences per plant in mid May.

Durability: Good stability of flower color, no pink hue.

Lastingness of the individual flower: About 8–9 days at 18° C.

Fragrance: None.

Pest/disease susceptibility/resistance: No observations to date.

PLANT

Foliage:
- *Shape*.—Kidney-shaped, with cordate, open base, and weak lobes.
- *Margin*.—Bicrenated.
- *Texture*.—Upper surface smooth, slightly glossy.
- *Size of leaf*.—100.5 mm wide, 57.5 mm long.
- *Color of upper surface*.—Dark-green, approximately RHS 137 A to 137 B.
- *Zonation*.—On young leaves, deep green color, RHS 147 A.
- *Color of lower surface*.—RHS 137 C.
- *Petioles*.—44–55 mm long, 2–3 mm diameter, green in color, approximately RHS 137 C.

General appearance and form:
- *Stem color*.—Light green, RHS 143 C.
- *Internode length*.—10–30 mm.
- *Branching pattern*.—8.8 branches.
- *Plant size*.—Height of foliage canopy 28.2 cm, width 42.0 cm, as measured from the top of the soil (base of the main stem) to the surface of the foliage canopy, without inflorescences.

I claim:

1. A new and distinct cultivar of geranium plant named 'Fistablanc', as described and illustrated herein.

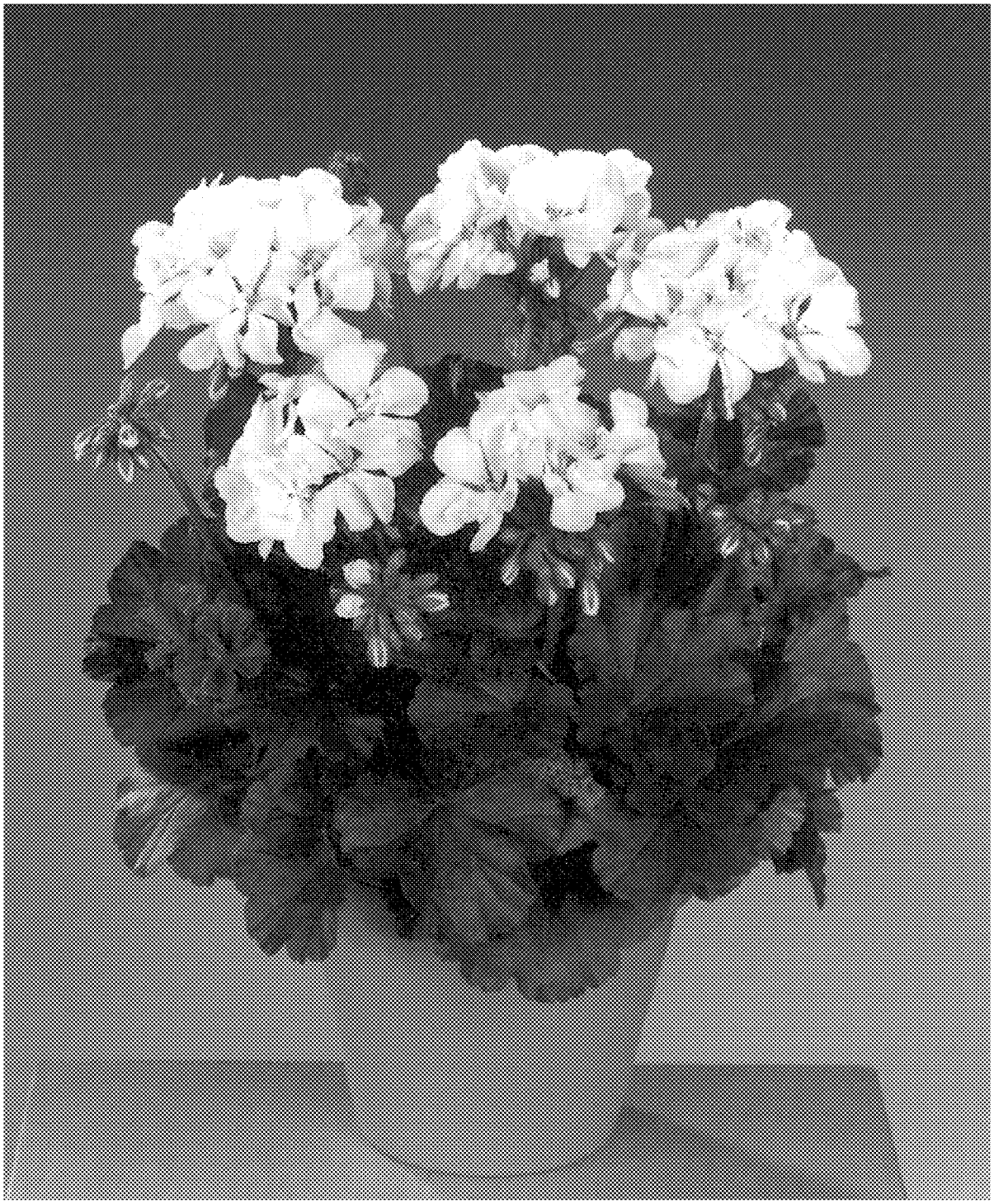

* * * * *